United States Patent [19]
Anthony et al.

[11] Patent Number: 4,857,545
[45] Date of Patent: Aug. 15, 1989

[54] DIBENZO-P-DIOXANES USEFUL AS FUNGICIDES

[75] Inventors: Vivienne M. Anthony, Maidenhead; John M. Clough, Marlow; Christopher R. A. Godfrey, Bracknell, all of United Kingdom

[73] Assignee: Imperial Chemical Industries PLC, London, England

[21] Appl. No.: 119,485

[22] Filed: Nov. 12, 1987

[30] Foreign Application Priority Data

Nov. 11, 1986 [DK] Denmark ............................ 4792/85
Dec. 3, 1986 [GB] United Kingdom ................ 8628924

[51] Int. Cl.$^4$ .................... A01N 43/32; C07D 319/24
[52] U.S. Cl. ..................................... 514/452; 549/359
[58] Field of Search ........................ 549/359; 514/452

[56] References Cited

FOREIGN PATENT DOCUMENTS 0178826 4/1986 European Pat. Off. .

*Primary Examiner*—Nicky Chan
*Attorney, Agent, or Firm*—Cushman, Darby & Cushman

[57] ABSTRACT

Compounds of the formula:

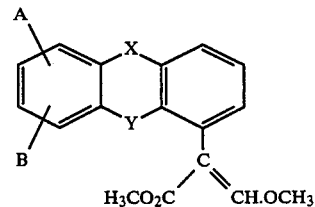

and stereoisomers thereof, wherein X and Y, which may be the same or different, are oxygen or sulphur; A and B, which may be the same or different, are hydrogen, halogen, alkyl, alkoxy, optionally substituted phenyl, optionally substituted phenoxy, or optionally substituted benzyloxy.

The compounds are useful as fungicides and also as plant growth regulators.

6 Claims, No Drawings

DIBENZO-P-DIOXANES USEFUL AS FUNGICIDES

This invention relates to derivatives of propenoic acid useful in agriculture (especially as fungicides but also as plant growth regulators), to processes for preparing them, to fungicidal compounds containing them, and to methods of using them to combat fungi, especially fungal infections in plants, and to regulate plant growth.

The invention provides a compound having the general formula (I):

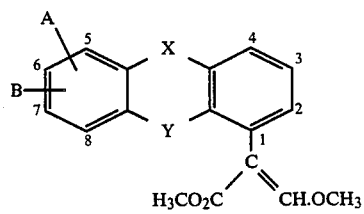

and stereoisomers thereof, wherein X and Y, which may be the same or different, are oxygen or sulphur; and A and B, which may be the same or different, are hydrogen, halogen, alkyl, alkoxy, optionally substituted phenyl, optionally substituted phenoxy, or optionally substituted benzyloxy.

When A or B, or both, are phenyl, phenoxy or benzyloxy groups, substituents which may be present on the phenyl rings include one or more of the following: halogen, $C_{1-4}$ alkyl, $C_{1-4}$ alkoxy, halo($C_{1-4}$)alkyl, cyano and nitro. When A or B or both are alkyl or alkoxy groups they are preferably $C_{1-4}$ alkyl or $C_{1-4}$ alkoxy groups. Preferred halogen substituents are chlorine and fluorine.

Compounds of particular interest are those in which A and B are both hydrogen and X and Y are the same; either both oxygen or both sulphur. But the invention also includes compounds in which not both of A and B are hydrogen and also compounds in which one of X and Y is oxygen and the other is sulphur.

The compounds of the invention contain a carbon-carbon double bond, and are sometimes obtained in the form of mixtures of geometric isomers. However, these mixtures can be separated into individual isomers, and this invention embraces such isomers.

The individual isomers which result from the unsymmetrically substituted double bond of the propenoate group are hereinafter identified by the commonly used terms "E" and "Z". These terms are defined according to the Cahn-Ingold-Prelog system which is fully described in the literature (see, for example, J March, "Advanced Organic Chemistry," 3rd edition, Wiley-Interscience, page 109 et seq).

Examples of the compounds of the invention are listed in Table I below.

TABLE I

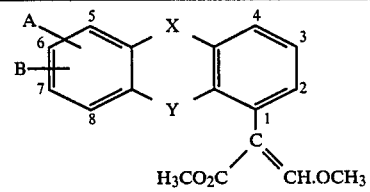

| COMPOUND NO. | X | Y | A | B | MELTING POINT (°C.) | ISOMER* |
|---|---|---|---|---|---|---|
| 1 | O | O | H | H | 109–110 | E |
| 2 | O | O | H | H | 113–114 | Z |
| 3 | S | S | H | H | 134–135 | E |
| 4 | S | S | H | H | 104–105 | Z |
| 5 | O | S | H | H | | E |
| 6 | O | S | H | H | | Z |
| 7 | S | O | H | H | 120–122.5 | E |
| 8 | S | O | H | H | | Z |
| 9 | O | O | 7-Cl | H | | E |
| 10 | S | S | 6-Cl | 7-Cl | | E |
| 11 | S | O | 7-C$_6$H$_5$ | H | | E |
| 12 | O | S | 7-CH$_3$O | H | | E |
| 13 | O | O | 6-Cl | 7-CH$_3$O | | E |
| 14 | S | S | 6-C$_6$H$_5$CH$_2$O | H | | E |
| 15 | S | O | 7-C$_6$H$_5$CH$_2$O | H | | E |
| 16 | O | S | 7-Br | H | | E |
| 17 | O | O | 7-(3-Cl—C$_6$H$_5$)O | H | | E |
| 18 | S | S | 6-F | 7-F | | E |
| 19 | S | O | 6-CH$_3$O | 7-CH$_3$O | | E |
| 20 | O | S | 7-CH$_3$ | H | | E |
| 21 | O | O | 7-Cl | 8-Cl | | E |
| 22 | S | S | 7-CH$_3$CH$_2$O | H | | E |
| 23 | S | O | 7-C$_6$H$_5$O | H | | E |
| 24 | O | S | 6-Cl | H | | E |
| 25 | O | O | 7-(CH$_3$)$_3$CO | H | | E |
| 26 | S | S | 7-Cl | H | | E |
| 27 | S | O | 6-CH$_3$O | 7-Cl | | E |
| 28 | O | S | 7-(CH$_3$)$_2$CH | H | | E |

*Geometry of the beta-methoxypropenoate group.

The compounds of the invention can be prepared from compounds of general formula (IV) by the steps shown in Scheme I. Throughout Scheme I the terms X and Y are as defined above except where otherwise specified, and A and B are as defined above.

Thus compounds of formula (I) can be prepared by treatment of methyl ketoesters of general formula (II) with the phosphorane of formula (C₆H₅)₃P:CH.OCH₃ in a suitable solvent such as an ether (see, for example, EP-A-0044448).

Methyl ketoesters of general formula (II) can be prepared by treatment of a lithiated species (III) with dimethyl oxalate in a suitable solvent such as an ether (for example, diethyl ether or tetrahydrofuran). Preferably, a tetrahydrofuran solution of the lithiated species is added to a tetrahydrofuran solution of dimethyl oxalate, cooled to a temperature below 0° C., for example −10° C. (see, for example, L. M. Weinstock, R. B. Currie and A. V. Lovell, *Synth. Commun.* 1981, 11, 943).

The lithiated species (III) can be prepared by direct lithiation of compounds (IV) using a strong lithium base such as n-butyl-lithium. Lithiation of phenoxyathiin occurs ortho to the C—O bond rather than the C—S bond to give the lithiated species (III) wherein X is sulphur and Y is oxygen. By contrast, lithiation of the 10-oxide or 10,10-dioxide derivatives of phenoxyathiin occurs ortho to the C—S bond to give a species (III) wherein X is oxygen and Y is SO or SO₂ respectively (see, for example, "Comprehensive Heterocyclic Chemistry", Editors A. R. Katritzky and C. W. Rees, Vol. 3, Chapter 2.26, page 975, Pergamon Press, 1984, and references therein). Reaction of these lithio-species with dimethyl oxalate as described above then gives methyl ketoesters (III) wherein X is oxygen and Y is SO or SO₂. Reduction of these oxidised sulphur bridging groups, either before or after reaction with the ylide (C₆H₅)₃P:CH.OCH₃, then provide compounds of formula (I) wherein X is oxygen and Y is sulphur.

Lithiation of certain compounds (IV) wherein A or B (or both) are not hydrogen can give regioisomeric mixtures of the derivatives (III). In such cases, alternative approaches to the compounds of the invention are probably preferred.

The compounds of general formula (IV) wherein X=Y=O; X=Y=S; X=O; Y=S; X=O, Y=SO; and X=O, Y=SO₂, can be prepared by methods described in the literature (see, for example, 'Comprehensive Heterocyclic Chemistry', Editors A. R. Katritzky and C. W. Rees, Vol. 3, Chapter 2.26, pages 984–986; 'Rodds's Chemistry of Carbon Compounds', 2nd Edition, Editor S. Coffey, Vol. IV, part H, pages 387, 407 and 424; and references therein.

Scheme I

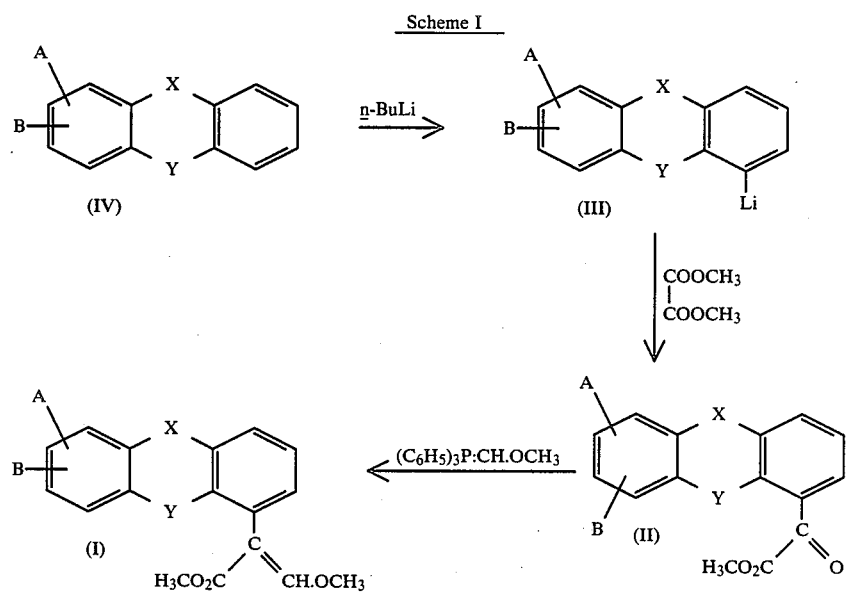

Scheme II

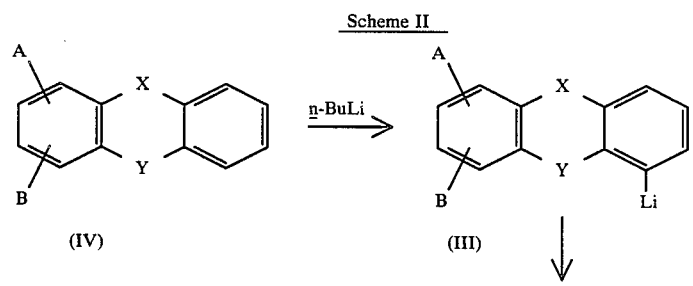

Scheme II

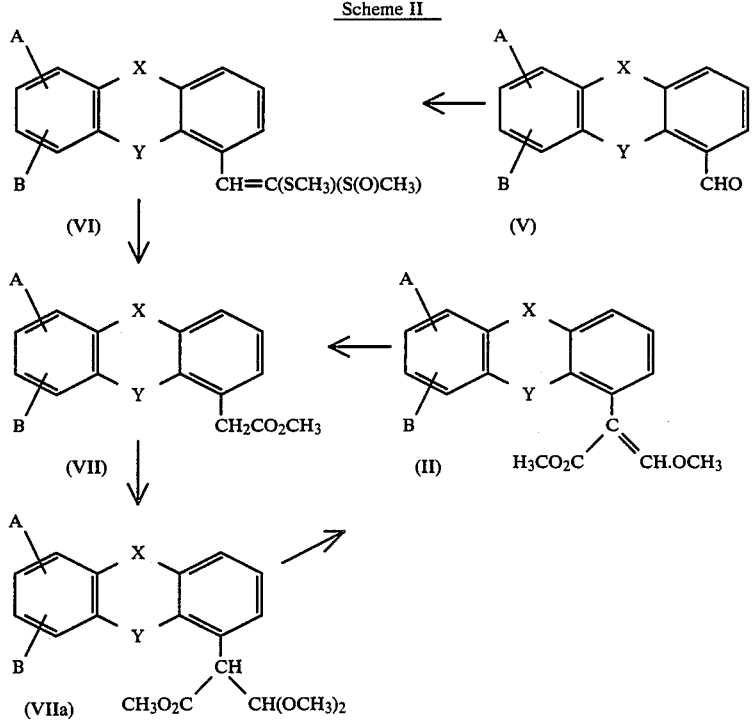

The compounds of the invention can also be prepared by the steps shown in scheme II. Throughout Scheme II the terms X, Y, A and B are as defined above.

Thus compounds of formula (I) may be prepared from acetates of general formula (VII) by treatment with methyl formate and a base followed by O-methylation, or from acetals of general formula (VIIa) by the elimination of the elements of methyl alcohol under acidic or basic conditions. [Both of these methods are described in detail in EP-A-No. 0178826, as is the general procedure for preparing the acetals of formula (VIIa)].

Acetates of general formula (VII) may be prepared from compounds of general formula (VI) by treatment with acidic methanol. Compounds of general formula (VI) may in turn be prepared from compounds of general formula (V) by reaction with methyl methylsulphinylmethyl sulphide and a base.

The aldehydes of general formula (V) may be prepared by reaction of the lithium species of general formula (III) already described in Scheme I, with a formyl transfer reagent such as N,N-dimethylformamide or N-formylmorpholine, in a suitable solvent such as THF, at a temperature of −70° to +20° C. but preferably at −20° to 0° C.

Scheme III

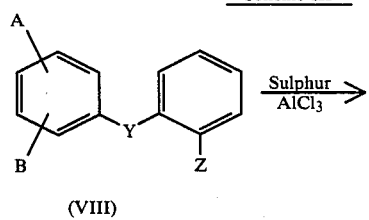

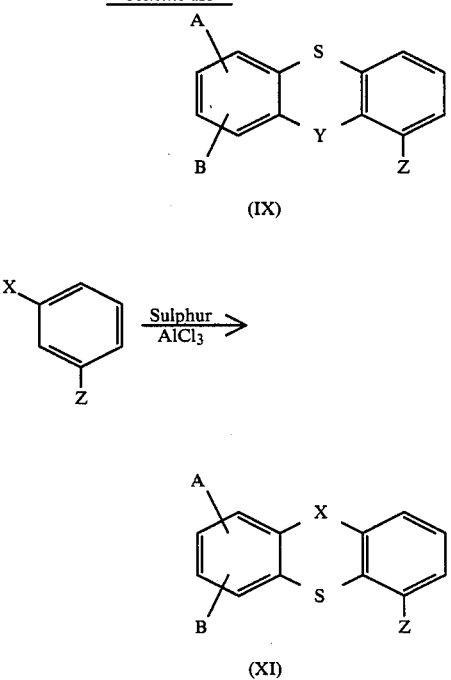

Compounds of the invention wherein at least one of the groups X and Y is sulphur can be made via reactions of the type shown in Scheme III. In Scheme III, the terms X, Y, A and B are as defined above, and the term Z represents the group CH₃O₂C.C:CH.OCH₃ of the compounds of the invention (I), or a group which can be transformed into such a group by the methods described above, or by methods described in the chemical literature.

Thus compounds of the formulae (VIII) and (X) can be converted into compounds (IX) and (XI) respectively by treatment with elemental sulphur and a Lewis acid such as aluminium chloride (compare, for example, C. M. Suter and C. E. Maxwell, *Organic Syntheses, Coll.* Vol. 2, 485). The formation of regioisomeric products is possible in the conversion of (X) into (XI) and, when the substituents A and B are unsymmetrically positioned, also in the conversion of (VIII) into (IX).

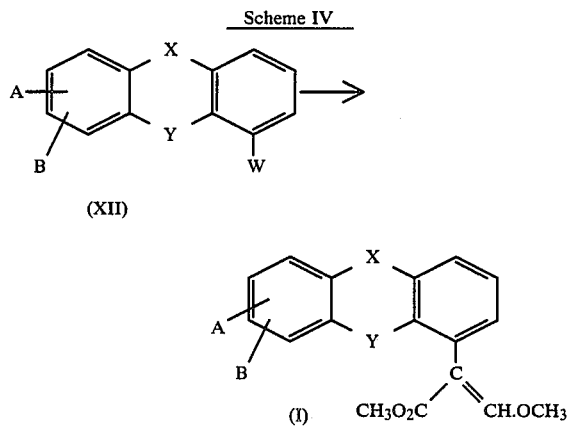

Scheme IV

There are, in addition, other ways in which the compounds of the invention of formula (I) may be made from appropriate precursors of formula (XII) in which the 3 fused rings are already present (Scheme IV). In Scheme IV the terms X, Y, A and B are as defined above, and the term W is a group which can be transformed into the group $CH_3O_2C.C:CH.OCH_3$ of the compounds of the invention (I) by the methods described above, or by methods described in the chemical literature.

Intermediates of formulae (VIII), (X) and (XII) may be prepared by methods described in the chemical literature.

In further aspects, the invention includes the process hereinbefore described for preparing the compounds of the invention and the intermediate compounds having the formulae (II), (III), (V), (VII) and (VIIa) used therein.

The compounds are active fungicides, and may be used to control one or more of the diseases:

*Pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as *Sphaerotheca macularis* on hops,

*Sphaerotheca fuliginea* on cucurbits (e.g. cucumber),

*Podosphaera leucotricha* on apples and *Uncinula necator* on vines.

Helminthosporium spp., Rhynchosporium spp., Septoria spp. and *Pseudocercosporella herpotrichoides* and on cereals.

*Cercospora arachidicola* and *Cercospridium personata* on peanuts and other Cercospora species on other hosts for example sugar beet, bananas, soya beans and rice.

*Botrytis cinerea* (grey mould) on tomatoes, strawberries, vegetables, vines and other hosts.

Alternaria species on vegetables (e.g. cucumber), oil seed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soybeans, tobacco, onions and other hosts. *Pseudoperonospora humuli* on hops and *Pseudoperonospora cubensis* on cucurbits, *Phytophthora infestans* on potatoes and tomatoes and other Phytophthora spp. on vegetables, strawberries, avocado, pepper, ornamentals, tobacco, cocoa and other hosts.

Some of the compounds have also shown a broad range of activities against fungi in vitro. They may have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Therefore in another aspect the invention provides a method of combating fungi, which comprises applying to a plant, to a seed of a plant, or to the locus of the plant or seed, a fungicidally effective amount of a compound of formula (I) as hereinbefore defined, or a composition containing the same.

The compounds may also be useful as industrial (as opposed to agricultural) fungicides, e.g. in the prevention of fungal attack on wood, hides, leather and paint films.

Some compounds exhibit plant growth regulating activity and may be deployed for this purpose, at appropriate rates of application.

Therefore, in yet another aspect the invention provides a method of regulating plant growth which comprises applying to a plant, to a seed of a plant or to the locus of the plant or seed an effective amount of a plant growth regulating compound of formula (I).

The compounds may be used directly for agricultural purposes but are more conveniently formulated into compositions using a carrier or diluent. The invention thus provides a fungicidal or plant growth regulator composition comprising a compound of general formula (I) as hereinbefore defined, and an acceptable carrier or diluent therefor.

The compounds, can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carb-oxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, R151297, pyrazophos, ethirimol, ditalimfos, tridemorph, triforine, nuarimol, triazbutyl, guazatine, triacetate salt of 1,1′-iminodi-(octamethylene)-diguanidine, buthiobate, propiconazole, prochloraz, flutriafol, hexaconazole, (2RS, 3RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-yl-methyl)pentan-3-ol, fluzilazole, triadimefon, triadimenol diclobutrazol, fenpropimorph, pyrifenox, fenpropidin, chlorozolinate, diniconazol, imazalil, fenfuram, carboxin, oxycarboxin, methfuroxam, dodemorph, BAS 454, blasticidin S, kasugamycin, edifenphos, kitazin P, cycloheximide, phthalide, probenazole, isoprothiolane, tricyclazole, 4-chloro-N-(cyano(ethoxy)methyl)benzamide, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6- dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout these Examples, the term 'ether' refers to diethyl ether; chromatography was carried out using silica gel as the solid phase; magnesium sulphate was used to dry solutions; and reactions involving water- or air-sensitive intermediates were performed under an atmosphere of nitrogen in dried solvents.

Where shown, infrared and n.m.r. data are selective; no attempt is made to list every absorption. The following abbreviations are used throughout:

| p.p.m. = | parts per million | THF = | tetrahydrofuran |

-continued

| g = | gramme(s) | delta = | chemical shift with respect to tetramethylsilane |
| ml = | milliliter(s) | | |
| IR = | infrared | | |
| n.m.r. = | nuclear magnetic resonance | $CDCl_3$ = | duterochloroform |
| | | s = | singlet |
| m.p = | melting point | d = | doublet |
| DMF = | N,N,N—dimethylformamide | t = | triplet |
| | | m = | multiplet |

EXAMPLE 1

This Example illustrates the preparation of E- and Z-methyl 3-methoxy-2-(dibenzo-p-dioxin-1-yl)propenoate (compounds numbers 1 and 2 of Table I respectively).

n-Butyl-lithium (12.6ml of 2.5M solution in hexane) was added over 15 minutes to a stirred solution of dibenzo-p-dioxin (5.0 g; prepared from 2-chlorophenyl by the method of H Gilman and J. J. Dietrich, *J.Am.-Chem.Soc.*, 1957, 79, 1439) in a mixture of ether (15 ml) and THF (30 ml) at a temperature between 0° and 5° C. The resulting yellow solution was allowed to warm to room temperature and stirred for 5 hours, whereupon it darkened to a greenbrown colour. This solution was added over 15 minutes to a solution of dimethyl oxalate (6.42 g) in THF (50 ml) at −10° C. The mixture was allowed to warm to room temperature and was stirred for 30 minutes, then poured into water and extracted with ether. The ether extracts were dried then concentrated to give an orange oil (7.09 g). Unreacted dibenzo-p-dioxin was removed by Kugelrohr evaporative distillation to leave methyl (dibenzo-p-dioxin-1-yl)ketoacetate (5.11 g), 92% pure by gas chromatography, as an orange oil, IR (film): 1735, 1680 $cm^{-1}$, $^1H$ n.m.r. ($CDCl_3$): delta 4.01 (3H,s) p.p.m.

Potassium t-butoxide (5.6 g) was added to a stirred suspension of (methoxymethylene)triphenylphosphonium chloride (19.0 g) in dry ether (100 ml). After 20 minutes, a solution of methyl (dibenzo-p-dioxin-1-yl)ketoacetate (5.0 g) in THF (20 ml) was added in one portion to the resulting deep red ylide solution. When thin-layer chromatography indicated that the ketoester had almost all been consumed, the reaction mixture was poured into water (100ml) and the organic and aqueous layers were separated. The aqueous layer was extracted with further ether. The organic layer and ether extracts were combined, dried, concentrated, and purified by chromatography using ether/petrol (1:1) as eluant to give (i) recovered starting ketoester (421 mg) as a yellow oil, eluted first; (ii) the E-isomer of the title compound (1.18 g, 15% yield from dibenzo-p-dioxin) as a white solid, m.p. 109°–110° C., $^1H$ n.m.r. ($CDCl_3$, 270 MHz): delta 3.69 (3H,s), 3.84 (3H,s), 6.7–6.94 (7H,m), 7.55 (1H,s) p.p.m., eluted second; and (iii) the Z-isomer of the title compound (1.02 g, 13% from dibenzo-p-dioxin) as a white solid, m.p. 113°–114° C., $^1H$ n.m.r. ($CDCl_3$, 270 MHz): delta 3.70 (3H,s), 3.92 (3H,s), 6.62 (1H,s), 6.7–6.9 (7H,m) p.p.m., eluted third.

EXAMPLE 2

This Example illustrates the preparation of E- and Z-methyl 3-methoxy-2-(thianthren-1-yl)propenoate (compounds numbers 3 and 4 of Table I respectively).

By the procedure described in Example 1, thianthrene (commercially available) was converted into the E-isomer of the title compound, a pale yellow solid, m.p. 134°–135° C., $^1H$ n.m.r. ($CDCl_3$, 270 MHz): delta 3.69 (3H,s), 3.85 (3H,s), 7.12–7.28 (4H,m), 7.40–7.52 (3H,m), 7.64 (1H,s) p.p.m., and the Z-isomer of the title compound, a white solid, m.p. 104°–105° C., $^1$H n.m.r. (CDCl$_3$, 270 MHz): delta 3.69 (3H,s), 3.96 (3H,s), 6.57 (1H,s), 7.10–7.28 (4H,m), 7.38–7.52 (3H,m) p.p.m.

EXAMPLE 3

This Example illustrates the preparation of E-methyl 3-methoxy-2-(dibenzo-p-oxathiin-1-yl)propenoate (compound No. 7 of Table I).

n-Butyl-lithium (11.25 ml of 1.6M solution in hexane) was added dropwise over 5 minutes to a stirred solution of dibenzo-p-oxathiin (3.0 g; prepared from diphenyl ether by the method of C. M. Suter and C. E. Maxwell, *Organic Syntheses*, Coll. Vol. 2, 485) in THF (30 ml) at a temperature of between −10° and 0° C. After completion of the addition the reaction mixture was allowed to warm to room temperature and stirred for 4 hours. The solution was then cooled to −10° C. and a solution of N-formylmorpholine (2.07 g) in THF (20 ml) was added. After completion of the addition the reaction mixture was allowed to warm to room temperature, stirred for 1.5 hours, allowed to stand overnight, and then poured into water (200 ml). The mixture was extracted with ethyl acetate and the ethyl acetate extracts were washed with water, dried, and evaporated to give an orange semisolid. This solid was triturated with ether, and the insoluble material was filtered off. The filtrate was evaporated and the residue was triturated with a mixture of ethyl acetate and petroleum ether to give crystalline dibenzo-p-oxathiin-1-yl carboxaldehyde (1.1 g); IR (nujol mull): 1695 cm$^{-1}$, $^1$H NMR (CDCl$_3$): delta 6.90–7.20 (5H,m); 7.27(1H,d); 7.62 (1H,d), 10.59 (1H,s) ppm.

Dibenzo-p-oxathiin-1-yl carboxaldehyde (1.1 g) was stirred at room temperature in THF (40 ml) with methyl methylsulphinylmethyl sulphide (0.5 ml) and "Triton B" (0.75 ml; "Triton B" is a 40% solution of benzyltrimethylammonium hydroxide in methanol) was added. The mixture was refluxed under nitrogen for 4.5 hours, cooled, allowed to stand overnight and poured into water. The mixture was then extracted with ethyl acetate, and the extract was washed with water, dried and evaporated to give a yellow oil (1.70 g). Without purification, the oil was dissolved in methanol (25 ml) and cooled to 5° C. under nitrogen. Acetyl chloride (1.0 ml) was carefully added over several minutes and after the addition the mixture was warmed to room temperature and stirred for 1 hour. The mixture was then refluxed for several hours and then cooled to room temperature, poured into water, and extracted with ether. The ethereal extracts were washed with water and dried, and then evaporated to give a yellow oil (1.5 g). This oil was purified by column chromatography eluting with ether, giving methyl (dibenzo-p-oxathiin-1-yl)acetate as a yellow oil (1.23 g), IR (film): 1745 cm$^{-1}$, $^1$H NMR (CDCl$_3$): delta 3.69 (3H,s); 3.75 (2H,s); 6.90–7.20 (7H,m) ppm.

Sodium hydride (material obtained by washing 0.36 g of a 60% dispersion in oil with hexane) was suspended in DMF (10–15 ml) and was cooled to 0°–5° C. To the stirred suspension was added a mixture of methyl (dibenzo-p-oxathiin-1-yl) acetate (1.23 g) and methyl formate (2.7 g) in DMF (10 ml) over 5 minutes. Some frothing occurred and the solution became deep grass-green in colour. After completion of the addition, the reaction mixture was stirred at 0° C. for 30 minutes, then allowed to warm to room temperature and stirred for 3 hours and then poured into water. The mixture was washed with ether, acidified with 2M hydrochloric acid and extracted with ether. This ethereal extract was washed with water, dried and evaporated to give a yellow-brown oil (1.47 g).

Without purification, this oil (1.47 g) was dissolved in DMF (10 ml), and potassium carbonate (1.25 g) and dimethyl sulphate (0.57 g) were added successively. The mixture was stirred at room temperature for 30 minutes, allowed to stand for 3 days, poured into water containing a little dilute hydrochloric acid, and extracted with ethyl acetate. The ethyl acetate extract was washed with water, dried, and evaporated to give a yellow oil (1.55 g). The oil was purified by high performance liquid chromatography on silica gel, eluting with 1:1 ethyl acetate:hexane, to give the title compound as a pale yellow solid (0.979 g), mp. 120°–122.5° C. IR (nujol mull): 1715, 1638 cm$^{-1}$, $^1$H NMR (CDCl$_3$): delta 3.68 (3H,s); 3.84 (3H,s); 6.86 (1H,d); 6.96–7.16 (6H,m); 7.61 (1H,s) ppm.

EXAMPLE 4

This Example illustrates an alternative preparation of E-methyl 3-methoxy-2-(thianthren-1-yl)propenoate (compound number 3 of Table I).

By a method similar to that described in Example 3, thianthrene (40.0 g) was formylated by successive treatment with n-butyl-lithium (127 ml of 1.6M solution in hexane) and N-formylmorpholine to give, after work-up but without any form of purification, a yellow oil comprising 1-formylthianthrene and unreacted thianthrene (91:9 by gas chromatography), IR (film): 1687 cm$^{-1}$; $^1$H NMR (CDCl$_3$): delta 10.58 (1H,s) ppm. This crude aldehyde was converted by the 2 steps described in Example 3, that is, by treatment with methyl methylsulphinylmethyl sulphide and "Triton B" followed by acidic methanolysis, into methyl (thianthren-1-yl)acetate (30.0 g, 56% yield from thianthrene) as a pale yellow solid, mp. 124°–125° C., IR (nujol mull): 1735 cm$^{-1}$; $^1$H NMR (CDCl$_3$) delta 3.73 (3H,s); 3.94 (2H,s) ppm.

Methyl (thianthren-1-yl)acetate (30.0 g) was converted by the 2 steps described in Example 3, that is, by successive treatment with sodium hydride and methyl formate then potassium carbonate and dimethyl sulphate, into the title compound (19.72 g, 57% yield) as a solid with mp. and spectroscopic data as described in Example 2 for the same compound.

The following are examples of compositions suitable for agricultural and horticultural purposes which can be formulated from the compounds of the invention. Such compositions form another aspect of the invention.

EXAMPLE 5

An emulsifiable concentrate is made up by mixing the ingredients, and stirring the mixture until all the constituents are dissolved.

| | |
|---|---|
| Compound No. 1 of Table I | 10% |
| Isophorone | 25% |
| Calcium dodecylbenzenesulphonate | 5% |
| Nonylphenolethoxylate (13 moles ethylene oxide) | 10% |
| Alkyl benzenes | 50% |

EXAMPLE 6

The active ingredient is dissolved in methylene dichloride and the resultant liquid sprayed on to the granules of attapulgite clay. The solvent is then allowed to evaporate to produce a granular composition.

| | |
|---|---|
| Compound No. 2 of Table I | 5% |
| Attapulgite granules | 95% |

EXAMPLE 7

A composition suitable for use as a seed dressing is prepared by grinding and mixing the three ingredients.

| | |
|---|---|
| Compound No. 3 of Table I | 50% |
| Mineral oil | 2% |
| China clay | 48% |

EXAMPLE 8

A dustable powder is prepared by grinding and mixing the active ingredient with talc.

| | |
|---|---|
| Compound No. 4 of Table I | 5% |
| Talc | 95% |

EXAMPLE 9

A suspension concentrate is prepared for chemicals which are largely insoluble solids by ball milling, for example, the constituents set out below, to form an aqueous suspension of the ground mixture with water.

| | |
|---|---|
| Compound No. 1 of Table I | 40% |
| Sodium lignosulphonate | 10% |
| Bentonite clay | 1% |
| Water | 49% |

This formula can be used as a spray by diluting into water or applied directly to seed.

EXAMPLE 10

A wettable powder formulation is made by mixing together the ingredients set out below and then grinding the mixture until all are thoroughly mixed.

| | |
|---|---|
| Compound No. 3 of Table I | 25% |
| Sodium lauryl sulphate | 2% |
| Sodium lignosulphonate | 5% |
| Silica | 25% |
| China clay | 43% |

EXAMPLE 11

The compounds were tested against a variety of foliar fungal diseases of plants. The technique employed was as follows.

The plants were grown in John Innes Potting Compost (No. 1 or 2) in 4 cm diameter minipots. The test compounds were formulated by bead milling with aqueous Dispersol T and diluted to the required concentration immediately before use. FOr the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (root drench) and to the foliage (by spraying) one or two days before the plant was inoculated with the disease. An exception was the test on *Erysiphe graminis hordei* in which the plants were inoculated 24 hours before treatment.

Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace $-5\%$ of disease on untreated plants
2 = 6–25% of disease on untreated plants
1 = 26–59% of disease on untreated plants
0 = 60–100% of disease on untreated plants The results are shown in Table II.

TABLE II

| COMPOUND NO. | PUCCINIA RECONDITA (WHEAT) | ERYSIPHE GRAMINIS (BARLEY) | VENTURIA INAEQUALIS (APPLES) | PYRICULARIA ORYZAE (RICE) | CERCOSPORA ARACHIDICOLA (PEANUTS) | PLASMOPARA VITICOLA (VINES) | PHYTOPHTHORA INFESTANS (TOMATOES) |
|---|---|---|---|---|---|---|---|
| 1 | 4 | 4 | 4 | 3 | 4 | 4 | 4 |
| 2 | 4 | 3 | 4 | 2 | 4 | 4 | 4 |
| 3 | 3 | 3 | 2 | 4 | 4 | 4 | 0 |
| 4 | 3 | 4 | 4 | 4 | 4 | 4 | 0 |

EXAMPLE 12

This Example illustrates the plant growth regulating properties of compounds 1, 2 and 3 of Table I when tested on a whole plant screen against two species of plant. The plant species are identified in Table III with the leaf stage at which they were sprayed.

A formulation of each chemical was applied at 4000 ppm (4 kg/ha in a 1000 l/ha field volume) using a track-sprayer and a SS8004E (Teejet) nozzle.

After spraying, the plants were grown in a glasshouse with 25° C. day/22° C. night temperatures. Supplementary lighting was supplied when necessary to provide an average photoperiod of 16 hours (14 hours minimum).

After 2–6 weeks in the glasshouse, depending on species and time of year, the plants were visually assessed for morphological characteristics against a control plant sprayed with a blank formulation. The results are presented in Table IV.

TABLE III

PLANT MATERIAL USED FOR WHOLE PLANT SCREEN

| Species | Code | Variety | Growth Stage at Treatment | No. Plants per 3" pot | Compost Type |
|---|---|---|---|---|---|
| Wheat | WW | Timmo | 1–1½ leaves | 4 | JIP* |
| Barley | BR | Atem | 1–1½ leaves | 4 | JIP* |
| Maize | MZ | Earliking | 2¼–2½ leaves | 1 | PEAT |
| Apple | AP | Red Delicious | 4–5 leaves | 1 | JIP* |
| Rice | RC | Ishikari | 2–2½ leaves | 4 | JIP* |

*John Innes Potting compost

TABLE IV

| Plant Material | Compound No. | R | G | A | T | I | P |
|---|---|---|---|---|---|---|---|
| WW | 1 | 1 | | | | | |
| WW | 2 | 1 | | | | 1 | |
| BR | 1 | | | | 1 | | |
| RC | 1 | 1 | | | | 1 | |
| RC | 3 | | 1 | | | | |
| AP | 1 | 2 | | | | | |
| AP | 2 | | | | | | 1 |
| MZ | 3 | | | 2 | | | |

KEY

R = Retardation
G = Greening effect
A = Apical damage
T = Tillering or side shooting
I = Interligular or internodal length reduction
P = Phytotoxicity All effects except phytotoxicity, are scored visually on a 1–3 basis where

1 = 10–30%
2 = 31–60%
3 = 61–100%

Blank means less than 10% effect. Phytotoxicity is scored on a 1–5 basis where

1 = less than 10%
2 = 11–30%
3 = 31–50%
4 = 41–70%
5 = greater than 70%

Blank means no effect at all observed.

We claim:

1. A compound having the general formula (I):

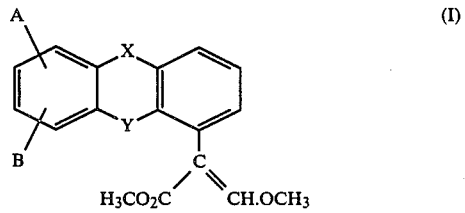

and stereoisomers thereof, wherein X and Y are both oxygen; and A and B, which are the same or different, are hydrogen, halogen, alkyl, alkoxy, phenyl, phenoxy, or benzyloxy, the phenyl rings of any of the foregoing groups being unsubstituted or substituted by one or more of the following: halogen, $C_{1-4}$ alkyl, $C_{1-4}$ alkoxy, halo ($C_{1-4}$)alkyl, cyano and nitro.

2. A compound according to claim 1 in which A and B are both hydrogen.

3. A compound according to claim 1 in which A and B are not both hydrogen.

4. A fungicidal or plant growth regulator composition comprising as an active ingredient a compound according to claim 1 and an acceptable diluent or carrier therefor.

5. A method of combating fungi or regulating plant growth which comprises applying to a plant, to a seed of a plant or to the locus of the plant or seed, a compound according to claim 1.

6. The E isomer of a compound according to claim 2.

* * * * *